United States Patent [19]

Clason et al.

[11] 4,308,154

[45] Dec. 29, 1981

[54] MIXED METAL SALTS AND LUBRICANTS AND FUNCTIONAL FLUIDS CONTAINING THEM

[75] Inventors: Donald L. Clason, Mentor; Calvin W. Schroeck, Eastlake, both of Ohio

[73] Assignee: The Lubrizol Corporation, Wickliffe, Ohio

[21] Appl. No.: 205,045

[22] Filed: Nov. 7, 1980

Related U.S. Application Data

[63] Continuation of Ser. No. 44,286, May 31, 1979, abandoned.

[51] Int. Cl.$^3$ .............................................. C10M 1/48
[52] U.S. Cl. ................................ 252/32.7 E; 252/35; 252/38; 252/46.7
[58] Field of Search ................... 252/46.7, 32.7 E, 35, 252/38

[56] References Cited

U.S. PATENT DOCUMENTS

| | | | |
|---|---|---|---|
| 2,923,682 | 2/1960 | Morway | 252/32.7 E |
| 3,000,822 | 9/1961 | Higgins et al. | 252/32.7 E |
| 3,271,310 | 9/1966 | Le Suer | 252/32.7 E X |
| 3,290,347 | 12/1966 | Miller | 252/32.7 E X |
| 3,347,790 | 10/1967 | Meinhardt | 252/32.7 E X |
| 3,489,682 | 1/1970 | Le Suer | 252/32.7 E X |
| 3,523,081 | 8/1970 | Braid | 252/32.7 E |
| 3,595,790 | 7/1971 | Norman et al. | 252/32.7 E |
| 3,625,893 | 12/1971 | Brook et al. | 252/32.7 E |
| 3,629,109 | 12/1971 | Gergel et al. | 252/32.7 E X |
| 3,726,798 | 4/1973 | Silver | 252/75 |

FOREIGN PATENT DOCUMENTS

| | | | |
|---|---|---|---|
| 959115 | 5/1964 | United Kingdom | 252/32.7 E |
| 1195041 | 6/1970 | United Kingdom | 252/32.7 E |

*Primary Examiner*—Andrew Metz
*Attorney, Agent, or Firm*—Ronald L. Lyons; William H. Pittman; Jack P. Ward

[57] ABSTRACT

Mixed metal salts (especially zinc salts) of dialkylphosphorodithioic acids and carboxylic acids, the ratio of equivalents of the dialkylphosphorodithioic to the carboxylic acid being between about 0.5:1 and about 4.5:1, are useful in lubricants and functional fluids (such as hydraulic fluids) as antioxidants and extreme pressure agents having improved thermal stability.

14 Claims, No Drawings

MIXED METAL SALTS AND LUBRICANTS AND FUNCTIONAL FLUIDS CONTAINING THEM

This application is a continuation of copending application Ser. No. 44,286, filed May 31, 1979 now abandoned.

This invention relates to phosphorus- and sulfur-containing compositions of improved thermal stability, useful in lubricants and functional fluids. In a general sense, the invention comprises mixed metal salts of (A) at least one acid of the formula

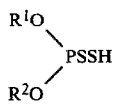

wherein each of $R^1$ and $R^2$ is a hydrocarbon-based radical, and (B) at least one aliphatic or alicyclic carboxylic acid; the ratio of equivalents of A to B being between about 0.5:1 and aout 4.5:1.

The use of metal salts, especially zinc salts, of phosphorodithioic acids as antioxidants and extreme pressure agents in lubricants and functional fluids has been known for some time. However, the environment in which such lubricants and functional fluids are used has become increasingly severe over recent years with the further development of machinery employing such lubricants and functional fluids. It is important, therefore, that materials of this type be developed which have higher thermal stability than has previously been the case.

A principal object of the present invention, therefore, is to produce compositions containing phosphorus, sulfur and metal which have high thermal stability and which also provide antioxidant and extreme pressure improving properties to lubricants and functional fluids.

A further object is to enable the incorporation of relatively large amounts of metal in such compositions.

Still another object is to provide improved lubricants and functional fluids, especially hydraulic fluids.

Other objects will in part be obvious and will in part appear hereinafter.

The mixed metal salts of this invention include those of the Group I metals, the Group II metals, aluminum, tin, cobalt, lead, molybdenum, manganese and nickel, as well as mixtures of two or more of those metals. The preferred salts are those of zinc.

As will be apparent from the foregoing, the mixed metal salts of this invention are salts of at least two acidic components of which component A is a phosphorodithioic acid. As used in the definition of that acid, the term "hydrocarbon-based radical" denotes a radical having a carbon atom directly attached to the remainder of the molecule and having predominantly hydrocarbon character within the context of this invention. Such radicals include the following:

(1) Hydrocarbon radicals; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like, as well as cyclic radicals wherein the ring is completed through another portion of the molecule (that is, the two indicated substituents may together form a cyclic radical). Such radicals are known to those skilled in the art; examples include methyl, ethyl, butyl, hexyl, octyl, decyl, dodecyl, tetradecyl, octadecyl, eicosyl, cyclohexyl, phenyl and naphthyl (all isomers being included).

(2) Substituted hydrocarbon radicals; that is, radicals containing non-hydrocarbon substituents which, in the context of this invention, do not alter predominantly hydrocarbon character of the radical. Those skilled in the art will be aware of suitable substituents (e.g., halo, hydroxy, alkoxy, carbalkoxy, nitro, alkylsulfoxy).

(3) Hetero radicals; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbon-based radical.

Preferably, the hydrocarbon-based radicals in the compounds useful as component A according to this invention are free from acetylenic and usually also from ethylenic unsaturation and have from about 3 to about 50 carbon atoms, desirably from about 3 to about 18 carbon atoms. $R^1$ and $R^2$ are most often identical, although they may be different and either or both may be mixtures. The radicals are usually hydrocarbon, preferably alkyl, and most desirably branched alkyl.

Component B is at least one aliphatic or alicyclic carboxylic acid. It may be a monocarboxylic or polycarboxylic acid, usually containing from 1 to about 3 carboxy groups and preferably only 1. It may contain from about 3 to about 40 and preferably from about 5 to about 20 carbon atoms.

The preferred carboxylic acids are those having the formula $R^3COOH$, wherein $R^3$ is an aliphatic or alicyclic hydrocarbon-based radical preferably free from acetylenic unsaturation. Suitable acids include the butanoic, pentanoic, hexanoic, octanoic, nonanoic, decanoic, dodecanoic, octadecanoic and eicosanoic acids, as well as olefinic acids such as oleic, linoleic, and linolenic acids and linoleic acid dimer. For the most part, $R^3$ is a saturated aliphatic radical and especially a branched alkyl radical such as the isopropyl or 3-heptyl radical. Illustrative polycarboxylic acids are succinic, alkyl- and alkenylsuccinic, adipic, sebacic and citric acids.

The mixed metal salts of this invention may be prepared by merely blending a metal salt of component A with a metal salt of component B in the desired ratio. This ratio is between about 0.5:1 and about 4.5:1 on an equivalent weight basis. Most often, the ratio is between about 2.5:1 and about 4.25:1. For this purpose, the equivalent weight of a phosphorodithioic acid is its molecular weight divided by the number of —PSSH groups therein, and that of a carboxylic acid is its molecular weight divided by the number of carboxy groups therein.

A second and preferred method for preparing the mixed metal salts of this invention is to prepare a mixture of the acids (components A and B) in the desired ratio and to react the acid mixture with a suitable metal base. When this method of preparation is used, it is frequently possible to prepare a salt containing an excess of metal with respect to the number of equivalents of acid present; thus, mixed metal salts containing as many as 2 equivalents and especially up to about 1.5 equivalents of metal per equivalent of acid may be prepared. The equivalent of a metal for this purpose is its atomic weight divided by its valence.

Variants of the above-described methods may also be used to prepare the mixed metal salts of this invention. For example, a metal salt of component A or B may be blended with the free carboxylic acid as component B or A, respectively, and the resulting blend reacted with additional metal base.

Suitable metal bases for the preparations of the mixed metal salts of this invention include the free metals previously enumerated and their oxides, hydroxides, alkoxides and basic salts. Examples are sodium hydroxide, sodium methoxide, sodium carbonate, potassium hydroxide, potassium carbonate, magnesium oxide, magnesium hydroxide, calcium hydroxide, calcium acetate, zinc oxide, zinc acetate, lead oxide, nickel oxide and the like.

The temperature at which the mixed metal salts of this invention are prepared is generally between about 30° and about 150° C., preferably up to about 125° C. If the mixed salts are prepared by neutralization of a mixture of acids with a metal base, it is preferred to employ temperatures above about 50° and especially above about 75°. It is frequently advantageous to conduct the reaction in the presence of a substantially inert, normally liquid organic diluent such as naphtha, benzene, xylene, mineral oil or the like. If the diluent is mineral oil or is physically and chemically similar to mineral oil, it frequently need not be removed before using the mixed metal salt as an additive for lubricants or functional fluids.

The preparation of the mixed salts of this invention is illustrated by the following examples. All parts and percentages are by weight.

EXAMPLE 1

A mixture of 67 parts (1.63 equivalents) of zinc oxide and 48 parts of mineral oil is stirred at room temperature and a mixture of 401 parts (1 equivalent) of di(2-ethylhexyl)phosphorodithioic acid and 36 parts (0.25 equivalent) of 2-ethylhexanoic acid is added over 10 minutes. The temperature increases to 40° C. during the addition. When addition is complete, the temperature is increased to 80° C. for 3 hours. The mixture is then vacuum stripped at 100° C. to yield the desired mixed metal salt as a 91% solution in mineral oil.

EXAMPLE 2

Following the procedure of Example 1, a product is prepared from 383 parts (1.2 equivalents) of a dialkyl phosphorodithioic acid containing 65% isobutyl and 35% amyl groups, 43 parts (0.3 equivalent) of 2-ethylhexanoic acid, 71 parts (1.73 equivalents) of zinc oxide and 47 parts of mineral oil. The resulting mixed metal salt, obtained as a 90% solution in mineral oil, contains 11.07% zinc.

EXAMPLE 3

Following the procedure of Example 1, a product is prepared from 474 parts (1.2 equivalents) of a dialkylphosphorodithioic acid containing 80% 2-ethylhexyl groups and 20% isobutyl groups, 43 parts (0.3 equivalent) of 2-ethylhexanoic acid, 80 parts (1.95 equivalents) of zinc oxide and 57 parts of mineral oil. The resulting mixed metal salt is obtained as a 91% solution in mineral oil.

EXAMPLE 4

A mixture of 118 parts (2.8 equivalents) of zinc oxide, 25 parts (0.25 equivalent) of sebacic acid and 72 parts of mineral oil is stirred at room temperature and a mixture of 584 parts (2 equivalents) of the dialkylphosphorodithioic acid of Example 2 and 36 parts (0.25 equivalent) of 2-ethylhexanoic acid is added over 30 minutes. The temperature increases to 65° C. during the addition. The solution is heated to 80° C. for 3 hours and vacuum stripped at 108° C. The residue is filtered to yield the desired mixed metal salt (90% solution in mineral oil) containing 11.7% zinc.

EXAMPLE 5

A product is prepared by the procedure of Example 1 except that an equivalent amount of oleic acid is substituted for the 2-ethylhexanoic acid.

As previously indicated, the mixed metal salts of this invention are useful as additives for lubricants and functional fluids, in which they function primarily as antioxidants and extreme pressure agents having improved thermal stability as compared with ordinary phosphorodithioic acid salts. They can be employed in a variety of lubricants based on diverse oils of lubricating viscosity, including natural and synthetic lubricating oils and mixtures thereof. The lubricants include crankcase lubricating oils for spark-ignited and compression-ignited internal combustion engines, including automobile and truck engines, two-cycle engines, aviation piston engines, marine and railroad diesel engines, and the like. Also contemplated are lubricants for gas engines, stationary power engines and turbines and the like. Transaxle lubricants, gear lubricants, metal-working lubricants and other lubricating oil and grease compositions, as well as functional fluids such as hydraulic fluids and automatic transmission fluids, benefit from the incorporation therein of the mixed metal salts of the present invention.

Natural oils include animal oils and vegetable oils (e.g., castor oil, lard oil) as well as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic oils include hydrocarbon oils and halo-substituted hydrocarbon oils such as polymerized and interpolymerized olefins [e.g., polybutylenes, polypropylenes, propylene-isobutylene copolymers, chlorinated polybutylenes, poly(1-hexenes), poly(1-octenes), poly(1-decenes), etc. and mixtures thereof]; alkylbenzenes [e.g., dodecylbenzenes, tetradecylbenzenes, dinonylbenzenes, di(2-ethylhexyl)benzenes, etc.]; polyphenyls (e.g., biphenyls, terphenyls, alkylated polyphenyls, etc.), alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc. constitute another class of known synthetic oils. These are exemplified by the oils prepared through polymerization of ethylene oxide or propylene oxide, the alkyl and aryl ethers of these polyoxyalkylene polymers (e.g., methyl-polyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$ Oxo acid diester of tetraethylene glycol.

Another suitable class of synthetic oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such neopentyl glycol, trimethylolpropane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic oils [e.g., tetraethyl silicate, tetraisopropyl silicate, tetra(2-ethylhexyl) silicate, tetra-(4-methyl-2-ethylhexyl) silicate, tetra-(p-tert-butylphenyl) silicate, hexa-(4-methyl-2-pentoxy)-disiloxane, poly(methyl)-siloxanes, poly(methylphenyl)siloxanes, etc.]. Other synthetic oils include liquid esters of phosphorus-containing acids (e.g., tricresyl phosphate, trioctyl phosphate, diethyl ester of decylphosphonic acid, etc.), polymeric tetrahydrofurans and the like.

Unrefined, refined and rerefined oils (and mixtures of each with each other) of the type disclosed hereinabove can be used in the lubricants and functional fluids of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment could be an unrefined oil. Refined oils are similar to the unrefined oils except they have been further treated in one or more purification steps to improve one or more properties. Many such purification techniques are known to those of skill in the art such as solvent extraction, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

Generally, the lubricants and functional fluids of the present invention contain an amount of the mixed metal salt sufficient to provide it with antioxidant and improved extreme pressure properties. Normally this amount will be about 0.25% to about 10%, preferably about 0.5% to about 7.5%, of the total weight of the fluid.

The invention also contemplates the use of other additives in combination with the mixed metal salts of this invention. Such additives include, for example, detergents and dispersants of the ash-producing or ashless type, corrosion- and auxiliary oxidation-inhibiting agents, pour point depressing agents, auxiliary extreme pressure agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-$\beta$-naphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

Ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the lubricants of this invention. The following are illustrative:

(1) Reaction products of carboxylic acids (or derivatives thereof) containing at least about 34 and preferably at least about 54 carbon atoms with nitrogen-containing compounds such as amine, organic hydroxy compounds such as phenols and alcohols, and/or basic inorganic materials. Examples of these "carboxylic dispersants" are described in British Patent No. 1,306,529 and in many U.S. patents including the following:

| | | |
|---|---|---|
| 3,163,603 | 3,351,552 | 3,541,012 |
| 3,184,474 | 3,381,022 | 3,542,678 |
| 3,215,707 | 3,399,141 | 3,542,680 |

-continued

| | | |
|---|---|---|
| 3,219,666 | 3,415,750 | 3,567,637 |
| 3,271,310 | 3,433,744 | 3,574,101 |
| 3,272,746 | 3,444,170 | 3,576,743 |
| 3,281,357 | 3,448,048 | 3,630,904 |
| 3,306,908 | 3,448,049 | 3,632,510 |
| 3,311,558 | 3,451,933 | 3,632,511 |
| 3,316,177 | 3,454,607 | 3,697,428 |
| 3,340,281 | 3,467,668 | 3,725,441 |
| 3,341,542 | 3,501,405 | Re 26,433 |
| 3,346,493 | 3,522,179 | |

(2) Reaction products of relatively high molecular weight aliphatic or alicyclic halides with amines, preferably polyalkylene polyamines. These may be characterized as "amine dispersants" and examples thereof are described for example, in the following U.S. Pat. Nos.:

| | |
|---|---|
| 3,275,554 | 3,454,555 |
| 3,438,757 | 3,565,804 |

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. Pat. Nos. are illustrative:

| | |
|---|---|
| 3,413,347 | 3,725,480 |
| 3,697,574 | 3,726,882 |
| 3,725,277 | |

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos.:

| | | | |
|---|---|---|---|
| 3,036,003 | 3,282,955 | 3,493,520 | 3,639,242 |
| 3,087,936 | 3,312,619 | 3,502,677 | 3,649,229 |
| 3,200,107 | 3,366,569 | 3,513,093 | 3,649,659 |
| 3,216,936 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |
| 3,281,428 | 3,455,832 | 3,600,372 | 3,708,522 |

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. Pat. Nos.:

| | |
|---|---|
| 3,329,658 | 3,666,730 |
| 3,449,250 | 3,687,849 |
| 3,519,565 | 3,702,300 |

The above-noted patents are incorporated by reference herein for their disclosures of ashless dispersants.

Auxiliary extreme pressure agents and corrosion- and auxiliary oxidation-inhibiting agents are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with terpentine or methyl oleate; phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; and metal thiocarbamates, such as zinc dioctyldithiocarbamate and barium heptylphenyl dithiocarbamate.

The mixed metal salts of this invention can be added directly to the lubricant. Often, however, they are preferably diluted with a substantially inert, normally liquid organic diluent such as mineral oil, naphtha, benzene, toluene or xylene, to form an additive concentrate. These concentrates usually contain from about 20% to about 90% by weight of the salt of this invention and may contain, in addition, one or more other additives known in the art or described hereinabove.

In the following table are listed exemplary lubricants (Examples C and D) and hydraulic fluids (Examples A and B) of this invention.

| Ingredient | Parts by weight Example | | | |
|---|---|---|---|---|
| | A | B | C | D |
| Mineral oil | 98.99 | 98.96 | 94.25 | 93.49 |
| Product of Example 1 | 0.97 | — | 1.50 | 1.00 |
| Product of Example 4 | — | 1.00 | — | — |
| Pentaerythritol ester of polybutenyl (mol.wt. about 1000) succinic acid, reacted with alkylene polyamine | — | — | 1.43 | — |
| Reaction product of alkylene polyamine with polybutenyl (mol. wt. about 1700) succinic anhydride containing more than one succinic group per polybutenyl group | — | — | 1.25 | 2.48 |
| Basic calcium petroleum sulfonate | — | — | — | 0.94 |
| Basic magnesium petroleum sulfonate | — | — | 0.39 | 0.24 |
| Basic sulfurized calcium tetrapropenyl phenate | — | — | 1.18 | — |
| Tetrapropenyl phenol sulfide | — | — | — | 1.46 |
| Oxypropylated tetrapropenyl succinic acid | 0.038 | 0.04 | — | — |
| Zinc dialkylphosphorodithioate | — | — | — | 0.39 |
| Polyoxyalkylene demulsifier | 0.0015 | — | — | — |
| Silicone anti-foam agent | — | — | 0.01 | 0.001 |

What is claimed is:

1. A mixed metal salt of (A) at least one acid of the formula

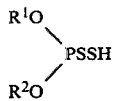

wherein each of $R^1$ and $R^2$ is a hydrocarbon-based radical, and (B) at least one carboxylic acid having the formula $R^3COOH$ which contains from about 5 to about 20 carbon atoms and wherein $R^3$ is an aliphatic or alicyclic hydrocarbonbased radical; the ratio of equivalents of A to B being between 2.5:1 and about 4.5:1; up to about 2 equivalents of metal being present per equivalent of acid; and the metal being at least one of Group I metals, Group II metals, aluminum, tin, cobalt, lead, molybdenum, manganese and nickel.

2. A mixed salt according to claim 1 wherein each of $R^1$ and $R^2$ is an alkyl raidcal containing from about 3 to about 50 carbon atoms.

3. A mixed salt according to claim 2 wherein each of $R^1$ and $R^2$ is a branched alkyl radical.

4. A mixed salt according to claim 1 wherein $R^3$ is a saturated aliphatic radical.

5. A mixed salt according to claim 4 wherein $R^3$ is a branched alkyl radical.

6. A mixed salt according to claim 1, 3, 4, 8 or 5 wherein the ratio of equivalents of A to B is between 2.5:1 and 4.25:1.

7. A mixed salt according to claim 1 wherein $R^3$ is an olefinic radical.

8. A mixed salt according to claim 7 wherein component B is oleic acid.

9. A mixed salt according to claim 1, 2, 3, 4, 5, 6, 10, 7 or 8 wherein the metal is zinc.

10. A mixed salt according to claim 6 wherein each of $R^1$ and $R^2$ is the 2-ethylhexyl radical and $R^3$ is the 3-heptyl radical.

11. An additive concentrate comprising a substantially inert, normally liquid organic diluent and from about 20% to about 90% by weight of a mixed salt according to claim 1, 2, 3, 4, 5, 6, 10, 7 or 8.

12. An additive concentrate comprising a substantially inert, normally liquid organic diluent and from about 20% to about 90% by weight of a mixed salt according to claim 9.

13. A lubricant or functional fluid comprising a major amount of a lubricating oil and about 0.25% to about 10% by weight of a mixed salt according to claim 1, 2, 3, 4, 5, 6, 10, 7 or 8.

14. A lubricant or functional fluid comprising a major amount of a lubricating oil and about 0.25% to about 10% by weight of a mixed salt according to claim 9.

* * * * *

UNITED STATES PATENT AND TRADEMARK OFFICE
CERTIFICATE OF CORRECTION

PATENT NO. : 4,308,154
DATED : December 29, 1981
INVENTOR(S) : Donald Lynn Clason and Calvin William Schroeck It is certified that error appears in the above—identified patent and that said Letters Patent is hereby corrected as shown below:

Column 9, line 12, "hydrocarbonbased" should be --hydrocarbon-based--. Column 10, line 1, "1, 3, 4, 8" should read --1, 2, 3, 4--.

Signed and Sealed this

Fifteenth Day of June 1982

[SEAL]

Attest:

GERALD J. MOSSINGHOFF

Attesting Officer    Commissioner of Patents and Trademarks